United States Patent
Dastillung et al.

(10) Patent No.: US 9,776,933 B2
(45) Date of Patent: Oct. 3, 2017

(54) PROCESS FOR PRODUCING 1,3-BUTADIENE FROM A FEEDSTOCK COMPRISING ETHANOL

(71) Applicants: IFP Energies nouvelles, Rueil-Malmaison (FR); Compagnie Generale des Etablissements Michelin, Clermont-Ferrand (FR); Michelin Recherche et Technique S.A., Granges-Paccot (CH)

(72) Inventors: Rejane Dastillung, Lyons (FR); Nicolas Cadran, Oullins (FR); Marc Jacquin, Lyons (FR); Raphael Huyghe, Saint Andeol le Chateau (FR); Beatrice Fischer, Lyons (FR)

(73) Assignees: IFP Energies Nouvelles, Rueil-Malmaison (FR); Compagnie Generale des Etablissements Michelin, Clermont-Ferrand (FR); Michelin Recherche et Technique S.A., Granges-Paccot (CH)

( * ) Notice: Subject to any disclaimer, the term of this patent is extended or adjusted under 35 U.S.C. 154(b) by 0 days.

(21) Appl. No.: 15/039,881

(22) PCT Filed: Nov. 28, 2014

(86) PCT No.: PCT/EP2014/076002
§ 371 (c)(1),
(2) Date: May 27, 2016

(87) PCT Pub. No.: WO2015/079040
PCT Pub. Date: Jun. 4, 2015

(65) Prior Publication Data
US 2016/0376206 A1  Dec. 29, 2016

(30) Foreign Application Priority Data
Nov. 29, 2013 (FR) .................... 13 61831

(51) Int. Cl.
*C07C 1/24* (2006.01)
*C07C 29/74* (2006.01)
(Continued)

(52) U.S. Cl.
CPC ............ *C07C 1/20* (2013.01); *C07C 1/207* (2013.01); *C07C 29/04* (2013.01);
(Continued)

(58) Field of Classification Search
CPC .................... C07C 1/24; C07C 29/74
(Continued)

(56) References Cited

U.S. PATENT DOCUMENTS

| 2,374,433 A | 4/1945 | Ipatieff |
| 2,474,874 A | 7/1949 | Van Der Hoeven |
| 6,323,383 B1 | 11/2001 | Tsuchida et al. |

FOREIGN PATENT DOCUMENTS

EP  1052234 A1  11/2000

OTHER PUBLICATIONS

International Search Report dated Feb. 10, 2015 issued in corresponding PCT/EP2014/076002 application (pp. 1-2).

*Primary Examiner* — Thuan D Dang
(74) *Attorney, Agent, or Firm* — Millen, White, Zelano and Branigan, P.C.

(57) ABSTRACT

Production of 1,3-butadiene ethanol, that is more than 50% of the total weight of feedstock:
A) conversion of feedstock and of ethanol effluent from separation B to a conversion effluent being a majority of 1,3-butadiene, water and ethylene, and to a hydrogen effluent, operating at a pressure between 0.1 and 1.0 MPa, a temperature between 300 and 500° C. in the presence of at least one catalyst;
B) separation of conversion effluent originating from A and hydration effluent from C to an ethanol effluent, a butadiene effluent, a water effluent and an ethylene effluent;

(Continued)

C) hydration of ethylene fed by ethylene effluent and/or water effluent both from separation B, to produce an ethanol hydration effluent then being recycled to separation B.

15 Claims, 1 Drawing Sheet

(51) Int. Cl.
  *C07C 1/20* (2006.01)
  *C07C 1/207* (2006.01)
  *C07C 29/04* (2006.01)
(52) U.S. Cl.
  CPC ...... *C07C 2521/06* (2013.01); *C07C 2521/08* (2013.01); *C07C 2521/10* (2013.01); *C07C 2523/20* (2013.01); *C07C 2523/26* (2013.01); *Y02P 20/582* (2015.11); *Y02P 30/42* (2015.11)
(58) Field of Classification Search
  USPC .................. 585/603, 609, 324, 903; 568/913
  See application file for complete search history.

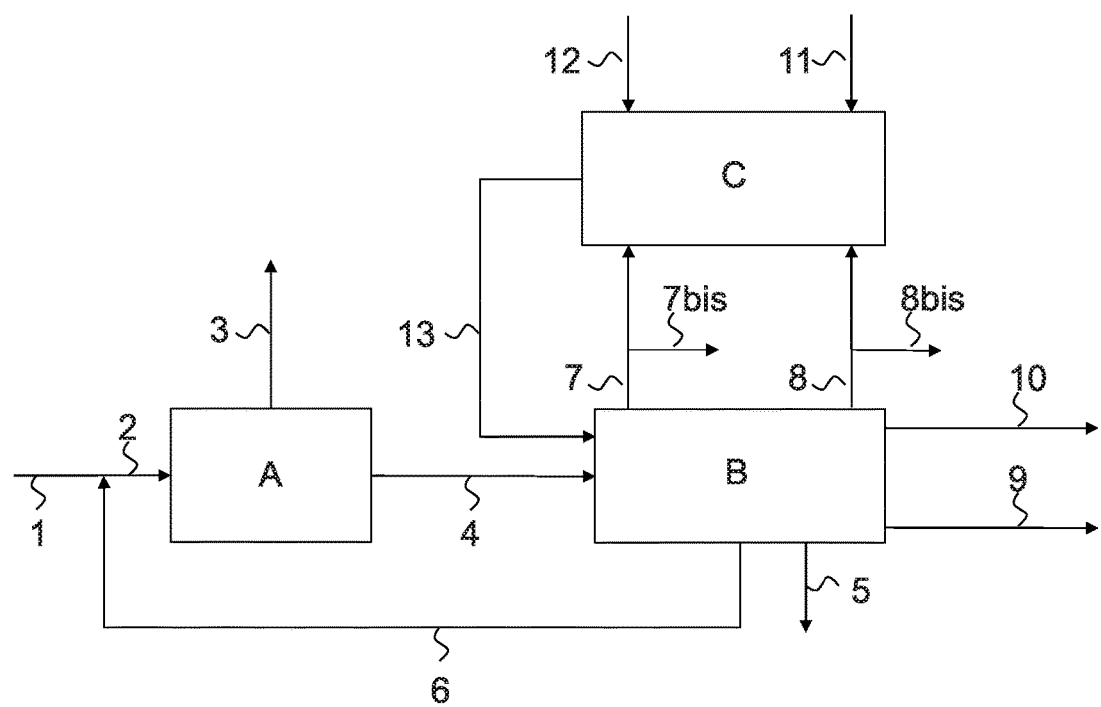

PROCESS FOR PRODUCING 1,3-BUTADIENE FROM A FEEDSTOCK COMPRISING ETHANOL

FIELD OF THE INVENTION

The invention relates to the field of the production of unsaturated hydrocarbons, in particular the production of diolefins, such as for example 1,3-butadiene, the latter being able to be used as a polymerization monomer, or converted to another chemical intermediate, such as for example 1,6-hexanediamine.

STATE OF THE PRIOR ART

The production of 1,3-butadiene from ethanol is well known to a person skilled in the art. Two processes have been industrialized on a large scale:
the "S.K." process, in which 1,3-butadiene is produced from ethanol in one reaction stage, with a single catalyst;
the "Carbide" process, in which ethanol is converted to acetaldehyde in a first reaction stage on a first catalyst consisting of a mixture of chromium oxide and copper oxide, followed by a second reaction stage on a second catalyst during which the ethanol-acetaldehyde mixture is converted to 1,3-butadiene (see for example U.S. Pat. No. 2,439,587).

The catalyst used in the "S.K." process is dehydrogenating, and therefore produces a significant quantity of acetaldehyde when it is fed with ethanol. Since the 1940's, the acetaldehyde produced has been recycled to the catalytic unit, allowing a significant improvement in yields. By means of this recycling, the catalytic unit of the "S.K." process therefore received an ethanol-acetaldehyde mixture.

The overall balance of the conversion reaction of ethanol to 1,3-butadiene is written as follows:

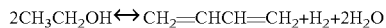

$$2CH_3CH_2OH \leftrightarrow CH_2=CHCH=CH_2 + H_2 + 2H_2O$$

For the sake of simplification, therefore when "feedstock rich in ethanol" is mentioned hereinafter, this term will denote the ethanol-acetaldehyde mixture comprising more than 50% by weight of ethanol sent to the single catalyst of the "S. K." process or to the second catalyst of the "Carbide" process.

Whatsoever the process (one stage or two), the selectivity of the conversion of the feedstock rich in ethanol to 1,3-butadiene is low, said conversion leading to the formation of numerous by-products. By by-product, is meant the constituents formed other than those produced or consumed by the main reaction (i.e. other than the 1,3-butadiene, $H_2$, $H_2O$ produced and the ethanol and acetaldehyde consumed). Toussaint et al., Industrial and Engineering Chemistry Vol. 39, No. 2, p. 120-125 1947 gives as an illustration of the distribution of the by-products formed in an industrial "Carbide" unit: diethyl ether (23% by weight of by-products), ethylene (11% by weight of by-products), hexenes and hexadienes (11% by weight of by-products). Nevertheless, the distribution of the by-products can change greatly depending on the operating conditions and the nature of the catalyst utilized for the conversion of the feedstock rich in ethanol to 1,3-butadiene.

Moreover, the conversion of the feedstock rich in ethanol to 1,3-butadiene is low. The unconverted reagents must therefore be separated from the products before being recycled. By way of illustration, the patent U.S. Pat. No. 2,393,381 describes the recycling of unconverted ethanol and acetaldehyde in the second catalytic section of the "Carbide" process. The patent U.S. Pat. No. 2,393,381 also describes the removal of the gaseous and liquid by-products generated by the catalytic process.

Numerous improvements have been made to the basic processes, in order to reuse certain by-products of this type of process. In fact, the by-products can be extracted by various separation processes, then:
either recycled to the catalytic unit producing 1,3-butadiene from the feedstock rich in ethanol.
or sent to a dedicated catalytic unit in order to be converted to other compounds.

Thus, in the patent U.S. Pat. No. 2,439,587 relating to the "Carbide" process, the ethyl acetate—a minor impurity of the process—is reused by recycling to the catalytic unit producing 1,3-butadiene. The ethyl acetate can be formed by different mechanisms within the catalytic unit, but can also produce 1,3-butadiene. In fact, under the conditions present within the catalytic unit, the ethyl acetate can replace the ethanol in order to produce 1,3-butadiene and acetic acid.

Another example well known to a person skilled in the art is the case of diethyl ether (DEE), a major by-product of the process. In the "S. K." process the DEE is returned to the catalytic section with the feedstock rich in ethanol. The recycling of the DEE to the catalytic unit makes it possible to improve the yield of 1,3-butadiene, and also leads to an increase in the quantity of ethylene produced. In fact, under the conditions present within the catalytic unit, the DEE can replace the ethanol in order to produce 1,3-butadiene and ethylene.

On the other hand, in the "Carbide" process, the recycling of the DEE to the catalytic unit does not lead to an increase in the yield of 1,3-butadiene. This difference in behaviour can be explained both by the nature of the catalyst and by the heat levels, which are different for the two processes. The DEE is therefore separated in the "Carbide" process (patent U.S. Pat. No. 2,474,874), then sent to a dedicated catalytic unit in order to be converted to another compound that can be reused, for example ethylene. In fact, the ethylene can be used as a raw material for the synthesis of styrene, which can itself be used as a raw material for the production of butadiene-styrene copolymer.

Another example of reuse disclosed in the patent U.S. Pat. No. 2,474,874 is the formation of ethanol by hydration of DEE. The ethanol produced can be recycled on site to the process for the production of 1,3-butadiene, so as to increase the overall yield.

The hydration of ethylene to ethanol corresponds to the following reaction balance:

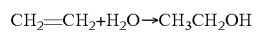

$$CH_2=CH_2 + H_2O \rightarrow CH_3CH_2OH$$

The processes for the hydration of ethylene to ethanol are well known to a person skilled in the art and divide into two major categories: direct and indirect hydration (Weissermel and Arpe, Industrial Organic Chemistry 4th edition, Wiley-VCH 2003).

Indirect hydration is characterized by the formation of reaction intermediates formed by the addition of an acid to the olefin, followed by hydrolysis to alcohol. This type of process can be carried out in the presence of concentrated sulphuric acid which, in the presence of gas containing ethylene, forms mono- and diethylsulphates, which decompose to ethanol after the addition of water to the medium. The advantages of this type of process are the low temperatures of the reactions (50-150° C.) and a high level of conversion per pass. The main disadvantage is the use of concentrated acid, which poses corrosion problems as well as significant operating costs for the re-concentration/reuse of the acid. Indirect hydration is carried out in a two-phase gas/liquid medium.

Direct hydration is characterized by the formation of alcohol in a single reaction stage. For the hydration of ethylene, the reaction is carried out in the gas phase. The reaction temperatures are higher (200-400° C.) and the conversion per pass is low (<10%) which requires significant recycling. This process uses heterogeneous catalysts based on inorganic acids such as phosphoric acid, deposited for example on silicic supports or those based on silica (kieselguhr etc.) which makes it possible to eliminate the problems associated with the use of a concentrated acid as required for the indirect hydration process. The drawbacks of this type of process are its low conversion per pass and the need to work with high-purity ethylene (in particular in order to avoid the accumulation of inerts during recycling).

The processes for the hydration of ethylene, whether direct or indirect, need to work with very pure ethylene. In fact, the presence of impurities is problematic for the correct operation of these processes. This can be illustrated with two typical impurities from the "$C_2$" distillation cut which are ethane and acetylene. In a direct hydration process, ethane accumulates as it is not converted. In a direct or indirect hydration process, the acetylene is converted to acetaldehyde, which must be managed and removed within the process.

Moreover, even with a high-purity ethylene, the ethanol produced must be purified. In fact, side reactions can occur and generate by-products such as for example acetaldehyde or diethyl ether.

Now, it was discovered that a judicious association of a stage for conversion of the ethanol to 1,3-butadiene and a stage for hydration of the ethylene to ethanol was possible, so as to increase the overall yield of 1,3-butadiene, despite a drop in the conversion and the selectivity in the hydration stage due to the use of an ethylene not as pure as that taught in the prior art.

Through the interplay of recyclings and synergies, said association makes it possible to reuse common by-products, whereas these by-products (for example DEE and acetaldehyde) must be removed when these stages are operated independently of one another.

SUMMARY AND ADVANTAGE OF THE INVENTION

An aspect of the invention is reusing the ethylene byproduct produced during the conversion of the feedstock rich in ethanol to 1,3-butadiene, in order to maximize the yield of 1,3-butadiene.

The ethylene by-product produced with 1,3-butadiene is concentrated in a gaseous flow which is hydrated in a dedicated catalytic section in order to produce a majority of ethanol. The effluent thus obtained is returned to within the stage of conversion to 1,3-butadiene via a separation stage which is able to separate the different constituents, for example the ethanol, water, DEE, acetaldehyde and ethylene. Thus, the ethylene impurity is reused, which makes it possible to maximize the overall yield of 1,3-butadiene.

This invention is particularly suitable when the quantity of ethylene produced is significant, due for example to the operating conditions, or to the catalyst utilized, or to the recycling of the diethyl ether within the unit for the conversion of the feedstock rich in ethanol to 1,3-butadiene.

Another aspect of the invention is to totally or partially feed the unit for the hydration of ethylene with another source of ethylene, in order to ensure greater flexibility to the operator of the unit for the production of 1,3-butadiene depending on the change in the cost of raw materials, the market price of the products and the price of energy. This other source of ethylene can for example be a unit for the steam cracking of fossil hydrocarbons or a Fluid Catalytic Cracking type unit.

Finally, another aspect of the invention is the total or partial use of the water coproduced with the 1,3-butadiene for hydrating the ethylene, whether this is a by-product generated within the process or originates from another source.

The applicant discovered that it was possible to feed the hydration unit with ethylene that is not as pure as that which is usually used in the prior art, while still obtaining an improvement in the overall performance of the process for the production of 1,3-butadiene, despite a hydration which functions sub-optimally.

The impact of the invention is felt in a reduction in the level of investment and the consumption of utilities with respect to the prior art (water, steam, electricity). In fact:

The ethanol produced by stage C of ethylene hydration does not need to be purified to 94.5% by mass, as is usually carried out in the prior art, as it is recycled as feedstock within the conversion stage A, where the purity requirement is lower.

The stages of separation and treatment of the effluents of stages A of conversion and C of hydration are pooled. There is thus no longer a requirement for a dedicated train for purification of the hydration effluent.

The acetaldehyde and the DEE produced by the ethylene hydration reaction are, in the state of the art, separated from the ethanol and most often flared, i.e. burnt off. As these products are also the reagents and by-products of the conversion stage A, it is longer necessary to have dedicated columns for drawing them off from the ethanol produced from the ethylene. The integration of the conversion stage A and the ethylene hydration stage C makes it possible to reuse the acetaldehyde and the DEE.

The ethylene produced by the conversion stage A and sent to the hydration unit does not need to be purified to the level of 99.9% by weight, which limits the losses produced and the levels of investment.

The water produced by the conversion stage A is totally or partially used in the hydration stage C, which limits discharges from the unit, and therefore the size and the consumption of utilities of the downstream water treatment unit.

DESCRIPTION OF THE INVENTION

The invention relates to a process for the production of 1,3-butadiene from a feedstock rich in ethanol, i.e. in which ethanol represents more than 50% of the total weight of said feedstock, comprising at least:

A) A stage of conversion of at least said feedstock rich in ethanol and of the ethanol effluent originating from separation stage B to a conversion effluent comprising a majority 1,3-butadiene, water and ethylene, and a hydrogen effluent, operating at a pressure comprised between 0.1 and 1.0 MPa, at a temperature comprised between 300 and 500° C. in the presence of at least one catalyst;

B) A stage of separation of at least said conversion effluent originating from A and the hydration effluent originating from C to at least one ethanol effluent, one butadiene effluent, one water effluent and one ethylene effluent;

C) A stage of hydration of the ethylene fed at least by said ethylene effluent and/or said water effluent both originating from separation stage B, in order to produce a hydration effluent comprising ethanol, said hydration effluent then being recycled to the separation stage B.

Feedstock Rich in Ethanol

According to the invention, the feedstock sent to the unit for the production of 1,3-butadiene is a feedstock rich in ethanol. By feedstock rich in ethanol, is meant a feedstock in which the ethanol represents more than 50% of the total weight of said feedstock.

Said feedstock rich in ethanol can advantageously comprise acetaldehyde. When said feedstock rich in ethanol comprises acetaldehyde, the mass ratio of ethanol to acetaldehyde is preferentially comprised between 2:1 and 4:1, preferably between 2.5:1 and 3.5:1 and very preferably 3:1.

Said feedstock rich in ethanol can also comprise impurities, such as for example ethers (diethyl ether, vinylethyl ether, methylethyl ether, butylethyl ether etc.), esters (for example ethyl acetate), acetals (for example ethyl acetal), aldehydes other than acetaldehyde and ketones (for example crotonaldehyde, butyraldehyde and acetone), alcohols (for example butanol, hexanol etc.), and saturated or unsaturated hydrocarbons. The content of these impurities is comprised between 0% and 20% of the total weight of the feedstock, preferably between 0 and 10% by weight.

Finally, said feedstock rich in ethanol can also comprise water. The water content is advantageously comprised between 0 and 30% of the total weight of the feedstock. Preferably, the water content is comprised between 4 and 15% by weight.

Stage A of Conversion of the Feedstock Rich in Ethanol to 1,3-butadiene

According to the invention, said feedstock rich in ethanol feeds a conversion stage A.

According to a preferred embodiment, said conversion stage A is operated in one reaction stage ("S.K." process). In this embodiment, said feedstock rich in ethanol is mixed with the ethanol effluent originating from the separation stage B before feeding said conversion stage A.

According to another preferred embodiment, said stage A is operated in two reaction stages, the first stage making it possible to convert the ethanol to acetaldehyde in the presence of a catalyst consisting of a mixture of chromium oxide and copper oxide, or of any other suitable catalyst. The mass ratio of ethanol to acetaldehyde in the effluent of said first reaction stage is preferentially comprised between 2:1 and 4:1, preferably between 2.5:1 and 3.5:1 and very preferably 3:1. In this embodiment, said feedstock rich in ethanol feeds the first reaction stage and the ethanol effluent originating from the separation stage B feeds the second reaction stage, in a mixture with said effluent from the first reaction stage.

Said feedstock rich in ethanol and the ethanol effluent originating from stage B undergo, in a conversion stage A, a chemical conversion so as to produce a conversion effluent and a hydrogen effluent. Said stage A totally or partially converts the feedstock rich in ethanol and the ethanol effluent originating from stage B to at least butadiene, ethylene, hydrogen, water, and acetaldehyde, including a majority of 1,3-butadiene. By majority, is meant that more than 50% by weight of the products formed (except the production of water, hydrogen and acetaldehyde) at the end of the stage A are 1,3-butadiene, preferably more than 60% by weight. Nevertheless, as the conversion of the feedstock rich in ethanol and of the ethanol effluent originating from stage B may be partial, 1,3-butadiene can represent less than 50% by weight of the conversion effluent (except for water, hydrogen and acetaldehyde) due, for example, to the presence of unconverted ethanol. Said conversion effluent comprises between 1 and 8% by weight of ethylene (except for water, ethanol, hydrogen and acetaldehyde).

Stage A is operated at a pressure comprised between 0.1 and 1.0 MPa, preferably between 0.1 and 0.5 MPa, preferably between 0.1 and 0.3 MPa. Stage A is operated at a temperature comprised between 300 and 500° C.

In the case where stage A is operated in one reaction stage, it is operated in the presence of a catalyst of zinc aluminate type or chromium-doped MgO—$SiO_2$ type, such as that used in the "S.K." process (see for example Bhattacharyya, Ganguly Journal of Applied Chemistry Volume 12, Issue 3, pages 97-110, March 1962). Stage A is then preferably operated at a temperature comprised between 380 and 430° C.

In the case where stage A is operated in two reaction stages, the second reaction stage of said stage A is operated in the presence of a catalyst of the silica type with an oxide of tantalum, zirconium or niobium, preferentially with 2% tantalum oxide, such as that used in the "Carbide" process (see for example Corson, Jones, Welling, Hinckley, Stahly, Ind. Eng Chem. 1950, 42, 2, 359-373). The second reaction stage of stage A is then preferably operated at a temperature comprised between 320 and 370° C. The first reaction stage of said stage A is operated according to the prior art, at a temperature comprised between 200 and 300° C.

A hydrogen effluent, comprising a majority of hydrogen, is separated at the end of the reaction by means known to a person skilled in the art (gas-liquid separator for example).

When the conversion stage A is implemented with two reaction stages (conversion according to the "Carbide" process), the hydrogen is mainly produced in the first reaction stage of the process. It is then separated between the two reaction stages.

Separation Stage B

According to the invention, the conversion effluent originating from stage A as well as the hydration effluent originating from stage C feed a separation stage B so as to produce at least one ethanol effluent, one butadiene effluent, one water effluent, and one ethylene effluent.

Said stage B makes it possible to separate the butadiene, the main product of the process according to the invention, as well as to produce an ethanol effluent capable of being recycled into conversion stage A.

By ethanol effluent, is meant an effluent comprising more than 50% by weight of ethanol. This effluent can contain up to 30% by weight of acetaldehyde. This effluent can also comprise impurities, such as for example ethers (for example diethyl ether, vinylethyl ether, methylethyl ether, butylethyl ether etc.), esters (for example ethyl acetate), acetals (for example ethyl acetal), aldehydes and ketones (for example crotonaldehyde, butyraldehyde and acetone), alcohols (for example butanol, hexanol etc.), and saturated or unsaturated hydrocarbons. The total content of these impurities is comprised between 0% and 20% by weight, preferably between 0 and 10% by weight. This effluent can also contain water. The water content can be comprised between 0 and 30% by weight. Preferably, the water content is comprised between 4 and 15% by weight. Acetaldehyde can advantageously be subsequently separated from the ethanol effluent.

Said ethanol effluent is recycled into stage A in a mixture with said feedstock rich in ethanol.

By butadiene effluent, is meant an effluent comprising more than 80% by weight, preferably more than 90% by weight, and preferably more than 99% by weight of 1,3-butadiene.

By water effluent, is meant an effluent comprising more than 90% by weight of water, preferably more than 99% by weight of water. This effluent can in particular contain impurities that are very polar and less volatile than water, in particular acetic acid.

By ethylene effluent, is meant a gaseous effluent at a temperature of less than 50° C. and a pressure of less than 0.8 MPa, comprising at least 50% by weight of ethylene. It can also comprise traces of hydrogen, carbon monoxide, carbon dioxide, propylene, acetylene, light alkanes (for example methane, ethane, propane), DEE, that may be formed by side reactions.

Separation stage B also advantageously produces an effluent of heavy gas oils, i.e. a gaseous effluent at a temperature of less than 50° C. and a pressure of less than 0.8 MPa comprising constituents other than those comprised in the ethylene effluent.

Separation stage B also advantageously produces an effluent of oils, i.e. an effluent comprising a mixture of saturated and unsaturated hydrocarbon compounds, and oxygenated compounds: esters, ethers, acetals, aldehydes, ketones, alcohols which can be saturated or unsaturated. This effluent is characterized by the fact that it is only composed of carbon, oxygen and hydrogen, and has a boiling point which can range from 20° C. to 500° C. It can be used as a fuel for the generation of utilities (heat, electricity) necessary for the correct operation of the process according to the invention, or be processed for separation operations in order to extract products therefrom that can be reused.

Separation stage B is carried out by a set of unit operations well known to a person skilled in the art, for example and non limitatively by distillation, cryogenic distillation, washing with solvent (for example water or ethanol), extractive distillation, liquid-liquid extraction, passing through a sieve, membrane separation. Thus, separation stage B is preferably chosen from the stages of: distillation, cryogenic distillation, washing with solvent, extractive distillation, liquid-liquid extraction, passing through a sieve, membrane separation and combinations of these stages.

Non-limitatively, an example of a sequence of these unit operations can be the following. The conversion effluent originating from stage A is cooled and sent into an ethanol washing column: an ethylene effluent, comprising ethylene, ethanol and optionally traces of hydrogen, is evacuated from the top of the washing column. The liquid effluent obtained at the bottom of the washing column is sent to a distillation column, in order to obtain an effluent rich in butadiene at the top of the distillation column. This effluent rich in butadiene is then washed with water in order to remove the volatile polar compounds. Finally, the effluent rich in butadiene having been washed with water is sent to an extractive distillation unit using a polar solvent (for example DMF, NMP or ACN) in order to remove the butenes and optionally other impurities so as to produce a butadiene effluent. The bottoms of the distillation column and washing columns are sent to a distillation train which makes it possible to produce a water effluent, an ethanol effluent, and an effluent of oils. The ethanol effluent can be recycled to conversion stage A, in a mixture with the feedstock rich in ethanol.

Hydration Stage C

According to the invention, at least a part of the ethylene effluent and/or at least a part of the water effluent originating from separation stage B feeds a hydration stage C so as to produce a hydration effluent.

Said stage C is advantageously fed by another external source of ethylene. Said other external source of ethylene can be, for example, a steam cracker or a unit of FCC type. Said stage C can also advantageously be fed by an external source of water.

The purity of the flow of ethylene feeding hydration stage C is therefore variable depending on the source of ethylene used. The purity of ethylene is comprised between 50 and 100%, preferably between 65 and 99.9% by weight, and very preferably between 65 and 75% by weight.

In a preferred embodiment, said hydration stage C is an indirect hydration. In a first stage, the ethylene reacts in the presence of concentrated sulphuric acid at a reaction temperature comprised between 50 and 150° C., in a two-phase gas/liquid medium. In a second stage, the products formed in the first stage are hydrolyzed in order to form a majority of ethanol at a temperature comprised between 70 and 100° C. Finally, the sulphuric acid is re-concentrated in order to be reused.

In another preferred embodiment, said hydration stage C is a direct hydration, carried out in gas phase, at a reaction temperature comprised between 200 and 400° C., in the presence of a heterogeneous catalyst based on inorganic acids such as phosphoric acid deposited for example on silicic supports or supports based on silica (kieselguhr etc.).

According to the invention, said hydration effluent is recycled to the separation stage B. It can either be mixed directly with the conversion effluent originating from conversion stage A, or treated with a dedicated unit operation in the separation stage B. This recycling makes it possible, ultimately, to recycle the ethanol to conversion stage A.

Said hydration effluent comprises, in addition to ethanol, DEE produced according to the following reaction:

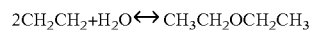

$$2CH_2CH_2 + H_2O \leftrightarrow CH_3CH_2OCH_2CH_3$$

Due to the low conversion (less than 15% of ethylene converted, preferentially less than 10%), the hydration effluent comprises, on the one hand, the gaseous by-products which have not totally reacted in the catalytic unit C (propylene acetylene, DEE), and on the other hand, the gaseous by-products which have not reacted (carbon monoxide, carbon dioxide, methane, ethane, propane) which are sent into separation stage B so as to keep the concentration of gaseous by-products not reacting in the feed of stage C constant.

In a preferred embodiment, all of the ethylene feeding the catalytic unit C is produced by conversion stage A, after passing into separation stage B. That is to say there is no feed by an external source of ethylene.

In this embodiment, the quantity of water produced in stage A is sufficient to allow the hydration of the ethylene produced in stage A. As a result, all of the water feeding hydration stage C can originate from conversion stage A, after separation in separation stage B.

Hydration stage C is also advantageously fed by ethylene originating from an external source.

If the quantity of water produced in stage A is not sufficient to hydrate the ethylene feeding hydration stage C, then an additional external source feeding water to stage C is also used. The part of the water originating from said external source represents less than 20% by weight, preferentially less than 10% by weight of the water feeding hydration stage C.

When the process according to the invention is implemented in a site comprising other processes, the flow of said site comprising acetylene or DEE can advantageously be treated in hydration stage C of the process according to the invention.

BRIEF DESCRIPTION OF THE FIGURE

The figure shows diagrammatically the process for the production of 1,3-butadiene from a feedstock rich in ethanol according to the invention.

The feedstock rich in ethanol 1 is mixed with the ethanol effluent 6 so as to form a conversion feedstock 2. Said conversion feedstock 2 is sent into conversion stage A so as to produce a conversion effluent 4 and a hydrogen effluent 3.

The conversion effluent 4 originating from stage A and the hydration effluent 13 originating from stage C feed the separation stage B in which an ethanol effluent 6, a butadiene effluent 5, a water effluent 7, an ethylene effluent 8, an effluent of heavy gases 9, and an effluent of oils 10 are separated.

A fraction 7a of the water effluent 7 is bled off. A fraction 8a of the ethylene effluent 8 is bled off. A part of the water effluent 7 and a part of the ethylene effluent 8 feed hydration stage C. An external source of ethylene 11 as well as an external source of water 12 also feed said stage C.

Stage C produces a hydration effluent 13, which feeds separation stage B.

The following examples illustrate the invention without limiting its scope.

EXAMPLES

In the following examples, the performances of the processes are evaluated on the basis of the overall yield of 1,3-butadiene defined as follows: mass flow rate of 1,3-butadiene in the butadiene effluent divided by the mass flow rate of ethanol in the feedstock rich in ethanol.

Example 1

Not According to the Invention

Example 1 illustrates the operation of the Lebedev process according to the prior art. After a conversion stage, the unconverted ethanol, as well as the unconverted acetaldehyde are separated and recycled upstream of said conversion stage.

A feedstock rich in ethanol constituted by 93.3% by weight of ethanol and 6.7% by weight of water feeds conversion stage A. The unconverted ethanol and acetaldehyde present in the conversion effluent are separated in a separation stage B and recycled upstream of stage A.

Separation stage B is operated so that 99% of the ethanol and 100% of the acetaldehyde comprised in the conversion effluent are recycled to stage A.

The overall yield of 1,3-butadiene of the process is 0.383.

Example 2

Not According to the Invention

This example is based on Example 1. After the conversion stage, an ethylene effluent is also separated which is hydrated in a hydration process as known to a person skilled in the art so as to produce a hydration effluent comprising ethanol. Said ethanol effluent is then recycled upstream of the conversion stage (after separation of the ethylene and a part of the water).

Conversion stage A is fed by a feedstock rich in ethanol identical to that of Example 1, as well as by a ethanol effluent originating from separation stage B.

Separation stage B is operated so that 99% of the ethanol and 100% of the acetaldehyde comprised in the conversion effluent are recycled to stage A.

As known by a person skilled in the art, the ethylene sent to the hydration unit must be very pure (Weissermel and Arpe, Industrial Organic Chemistry 4$^{th}$ edition, Wiley-VCH 2003). The separation and purification of the ethylene contained in said conversion effluent to an ethylene effluent comprising 99.9% by weight of ethylene leads to a 15% loss of ethylene. Thus, separation stage B makes it possible to recover 85% of the ethylene comprised in said conversion effluent.

Said ethylene effluent, as well as a flow of water the origin of which is external to the process, is converted to ethanol in a hydration process as known to a person skilled in the art. At the end of the hydration reaction stage, the ethanol is purified in a dedicated separation unit typical of the hydration processes of the prior art, which produces ethanol at 94.5% by weight, and recycled to the feed of conversion stage A.

The overall yield of the process is 0.395, i.e. 3.1% more than in Example 1.

Example 3

According to the Invention

In this example, according to the invention, the conversion effluent is treated in a separation stage B so as to produce at least one butadiene effluent, one ethanol effluent, one ethylene effluent and one water effluent. The purity specification of the ethylene effluent is lower, and a flow of water which is internal to the process is used for the hydration stage.

Conversion stage A is fed by a feedstock rich in ethanol identical to that of Example 1, as well as by an ethanol effluent originating from separation stage B.

Separation stage B, fed by the conversion effluent originating from said stage A, as well as by the hydration effluent originating from said stage C, makes it possible to produce at least one butadiene effluent, one ethanol effluent, one ethylene effluent and one water effluent. It is operated so that 99% of the ethanol and 100% of the acetaldehyde comprised in the feed of said stage B are recycled to stage A. 99% of the ethylene comprised in said conversion effluent is separated into said ethylene effluent. The purity of ethylene in this effluent is 73% by weight. It is sent, as well as said water effluent, to a hydration stage C The overall yield of the process is 0.397, i.e. 0.5% better than Example 2 and 3.7% better than Example 1.

With reference to Example 2, the overall performance of the process was able to be maintained, even improved by 0.5% even though the purity of the ethylene sent to the hydration stage is much lower (73% by weight instead of 99.9% by weight). The separation of the ethylene content in the conversion effluent originating from stage A is therefore facilitated, due to a less strict purity requirement, in the example according to the invention, which allows an improved recovery of said ethylene (99% instead of 85%).

This lower purity also leads to a separation that has lower energy consumption. Combining the treatment of the conversion effluent originating from stage A and the hydration effluent originating from stage C makes it possible to reduce the quantity of equipment required by 40%.

The process according to the invention therefore allows an improved reuse of the ethylene co-produced in conversion stage A, as 16.4% more ethylene is reused compared with Example 2 (99%/85%).

The hydration of a low-purity ethylene effluent, contrary to the uses known from the prior art, surprisingly has no detrimental effect on the overall yield of 1,3-butadiene of the process. In fact, even if the water effluent and the ethylene effluent which feed said hydration stage comprise impurities, such as for example acetic acid, acetaldehyde, acetylene, propylene and diethyl ether, combining the separation stage B capable of separating these compounds and the recycling to the conversion stage A which converts some of these impurities compensates for the deterioration in the performance of hydration stage C linked to the use of feedstock (effluent ethylene and water) which is not as pure as those usually used in the prior art.

The invention claimed is:

1. A process for the production of 1,3-butadiene from a feedstock rich in ethanol, in which the ethanol represents more than 50% of the total weight of said feedstock, comprising at least:
   stage A) conversion of at least said feedstock rich in ethanol and of ethanol effluent originating from separation stage B to a conversion effluent comprising a majority of 1,3-butadiene, water and ethylene, and to a hydrogen effluent, operating at a pressure of 0.1 to 1.0 MPa, at a temperature of 300 to 500° C. in the presence of at least one catalyst;
   stage B) separation of at least said conversion effluent originating from A and the hydration effluent originating from C to at least an ethanol effluent, a butadiene effluent, a water effluent and an ethylene effluent;
   stage C) hydration of the ethylene fed at least by said ethylene effluent and/or said water effluent both originating from stage B, in order to produce a hydration effluent comprising ethanol, said hydration effluent then being recycled to stage B.

2. The process according to claim 1, in which said stage A is operated at a pressure of 0.1 to 0.5 MPa.

3. The process according to claim 1, in which said stage A is operated in one reaction stage and in which said feedstock rich in ethanol is mixed with the ethanol effluent originating from stage B before feeding said stage A.

4. The process according to claim 3, in which said stage A is operated in the presence of a zinc aluminate catalyst or chromium-doped MgO—SiO$_2$ catalyst, at a temperature of 380 to 430° C.

5. The process according to claim 1, in which said stage A is operated in two reaction stages, a first reaction stage converting the ethanol to acetaldehyde in the presence of a catalyst at a mass ratio of ethanol to acetaldehyde in effluent of said first reaction stage being of 2:1 to 4:1, said feedstock rich in ethanol feeding said first reaction stage and said ethanol effluent originating from stage B feeding said second reaction stage, in a mixture with said effluent from said first reaction stage.

6. The process according to claim 5, in which the second reaction stage of stage A is operated in the presence of a catalyst of silica with an oxide of tantalum, zirconium or niobium, the second reaction stage of stage A being operated at a temperature of 320 to 370° C., the first reaction stage of said stage A being operated at a temperature of 200 to 300° C.

7. The process according to claim, in which stage B is: distillation, cryogenic distillation, washing with solvent, extractive distillation, liquid-liquid extraction, passing through a sieve, membrane separation or combinations thereof.

8. The process according to claim 1, in which said stage C is an indirect hydration, in which, in a first reaction stage, the ethylene reacts in the presence of concentrated sulphuric acid at a reaction temperature of 50 to 150° C., in a two-phase gas/liquid medium and in a second stage, the products formed in the first stage are hydrolyzed in order to form a majority of ethanol at a temperature of 70 and 100° C.

9. The process according to claim 1, in which said stage C is a direct hydration operating in gas phase, at a reaction temperature comprised between 200 and 400° C., in the presence of a heterogeneous catalyst based on inorganic acids.

10. The process according to claim 1, in which said feedstock rich in ethanol comprises acetaldehyde, at a mass ratio of ethanol to acetaldehyde of 2:1 to 4:1.

11. The process according to claim 1, in which the purity of the ethylene flow feeding hydration stage C is 65 to 99.9% by weight.

12. The process according to claim 1, in which the purity of the ethylene flow feeding hydration stage C is 65 to 75% by weight.

13. The process according to claim 5, wherein the catalyst is a mixture of chromium oxide and copper oxide.

14. The process according to claim 9, wherein the heterogeneous catalyst is phosphoric acid deposited on a silica-based support.

15. The process according to claim 1, wherein ethylene effluent is fed to stage C without further purification.

* * * * *